United States Patent [19]
Nowacki et al.

[11] Patent Number: 4,589,684
[45] Date of Patent: May 20, 1986

[54] ANESTHESIOLOGY CONNECTOR

[75] Inventors: Christopher Nowacki; Alfred Brisson, both of Arlington Heights, Ill.

[73] Assignee: Trutek Research, Inc., Arlington Heights, Ill.

[21] Appl. No.: 540,324

[22] Filed: Oct. 11, 1983

[51] Int. Cl.⁴ .............................................. F16L 39/00
[52] U.S. Cl. ................................... 285/319; 285/423; 285/921
[58] Field of Search ............... 285/319, 320, DIG. 22, 285/423

[56] References Cited

U.S. PATENT DOCUMENTS

| | | | |
|---|---|---|---|
| 373,825 | 11/1887 | Gleich et al. | 285/319 X |
| 2,453,741 | 11/1948 | Bopp | 285/319 X |
| 2,784,989 | 3/1957 | Corcoran | 285/319 X |
| 4,152,017 | 5/1979 | Abramson | 285/DIG. 22 |

FOREIGN PATENT DOCUMENTS 2328567 1/1975 Fed. Rep. of Germany ...... 285/319

Primary Examiner—Richard J. Scanlan, Jr.
Attorney, Agent, or Firm—Trexler, Bushnell & Wolters, Ltd.

[57] ABSTRACT

A female anesthesiology connector is provided for connecting a tube supplying anesthesiology gases to an endotracheal tube. The female connector is provided with a longitudinally extending finger having a bevelled locking tooth thereon for providing a positive securement of the male connector of an endotracheal tube with the present female anesthesiology connector. The finger in on a ring inserted into the body of the female connector and secured in place by means of sonic or solvent welding, or a suitable adhesive. The ring and the body together provide an internal groove receiving an O-ring which makes a positive seal with the male connector of the endotracheal tube.

2 Claims, 2 Drawing Figures

ANESTHESIOLOGY CONNECTOR

BACKGROUND OF THE INVENTION

It is common practice in the administration of anesthesia for surgery to utilize an endotracheal tube inserted through the patient's mouth into the trachea. The external end of this tube has a 1 degree taper and forms a friction fit with an anesthesia tube leading to a mixer for anesthetic gas and oxygen. The free end comprises a male component having standard dimensions of 22 mm. outside diameter and 15 mm. inside diameter. The male component is asssembled with a female component that may be in the form of an elbow, a straight tube, or a Y. It is common practice to reinforce the friction fit between the male and female members by wrapping adhesive tape around the connection.

Both the male and female components are commonly made of molded plastic material If great care is not exercised in the manufacture of the parts, there is the possibility of a leak. Furthermore, there are usually many people in the immediate vicinity of a patient in surgery, and the anesthesia tube or the endotracheal tube may be bumped, sometimes causing the junction between the male and female members to come apart, particularly if they have not been taped securely. A leak between malformed plastic parts or a leak generated by partial separation of the male and female members, or a total disassembly thereof is dangerous. A patient can die or suffer permanent brain damage in a rather short period of time if a leak of separation causes improper administration of anesthesia, while leaking gas can be dangerous to the surgical team.

OBJECTS AND SUMMARY OF THE PRESENT INVENTION

It is an object of the present invention to provide an anesthesia connector in the form of a female fitting forming a positive connection with the male fitting on the end of an endotracheal tube remote from the patient.

It is a further object of the present invention to provide such a female fitting having a manually releasable positive engagement with the male endotracheal tube connector.

Yet another object of the present invention is to provide a female fitting for connection to the male connector of an endotracheal tube utilizing an O-ring to compensate for any irregularities in plastic molding and to form a positive seal between the female and male fittings or connectors of an endotracheal tube.

In achieving the foregoing objects, we provide a female endotracheal tube connector or fitting having an inserted ring in the receiving end thereof, which ring is secured in place by sonic welding, adhesives, or the like, said ring forming with the female fitting a groove receiving an internal O-ring, and further having an extending latch finger thereon engageable with an external circumferential ring on the male fitting at the end of the endotracheal tube.

DRAWING DESCRIPTION

The invention will best be understood from the following description when taken in connection with the accompanying drawings wherein:

FIG. 1 comprises a longitudinal sectional view through a female anesthesiology connector constructed in accordance with the present invention; and FIG. 2 comprises a right end view of the connector.

DETAILED DESCRIPTION OF THE ILLUSTRATED EMBODIMENT

Figure 1:
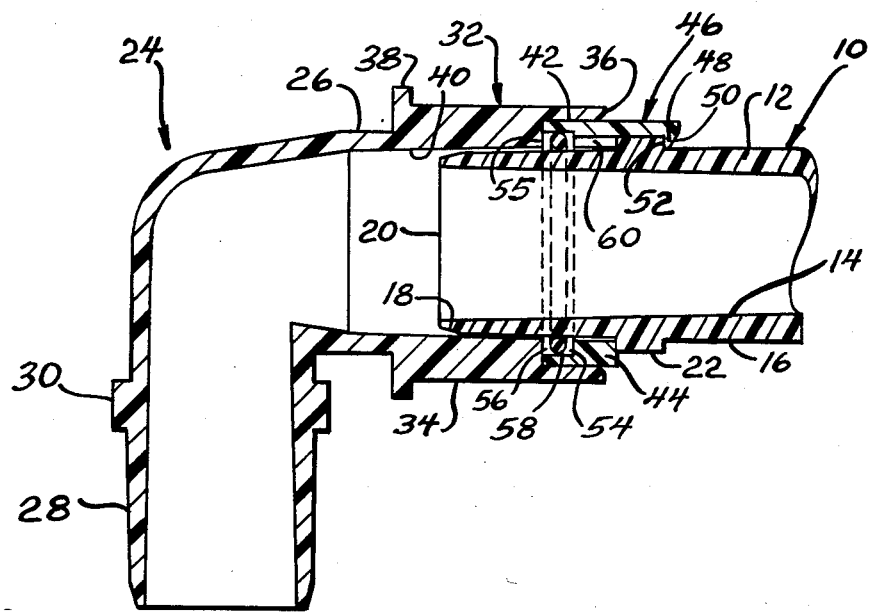
Figure 2:
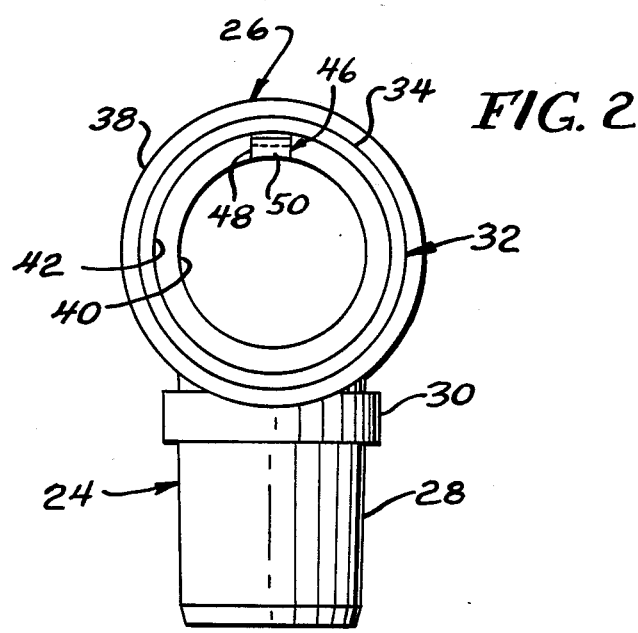

The end of an endotracheal tube which is remote from the patient is shown at 10 in FIG. 1, being omitted from FIG. 2 for clarity in illustration. Specifically, this portion of the endotracheal tube 10 includes a plastic molding 12 having a cylindrical inner bore 14 and an outer surface 16 tapering at 1 degree to a further entering taper 18 at the extreme end 20. Spaced some distance from the end 20 an integral collar 22 is provided on the external circumference of the male connector or fitting 12. This is common or universal practice with existing endotracheal tube male connectors and does not require any change for cooperation with the present invention.

The present invention is illustrated as comprising a female connector in the form of an elbow 24, but it will be understood that the principles of the invention are equally well adapted to a straight tube or a Y connector. The elbow 24 comprises a first tubular portion 26 for connection to the male fitting 12 and a second tubular portion 28 integral with the first tubular portion 26, and at right angles thereto. The second tubular portion has an external 1 degree taper and is provided with a circumferential collar 30. A flexible conduit to a mixer-valve for anesthesiology gases is connected to the second tubular portion 28 by suitable known means.

The first or right hand portion 26 (as viewed in FIG. 1) comprises a tubular female fitting 32 having a cylindrical outer surface 34 and a receiving end 36. At the opposite end of the cylindrical surface from the receiving end 36 there is provided a circumferentially extending flange 38 providing a convenient finger grip for pushing the female fitting 32 onto the male connector 12.

The female fitting 32 is provided with an internal bore 40 with a 1 degree taper conforming to the outer surface of the male fitting or connector 12. At the entering end 36 there is also a counterbore 42 cylindrical in nature and of somewhat greater diameter than the bore 40 and of greater depth than the offset between the bores 40, 42.

A retaining ring 44 has an outer diameter only very slightly less than the counterbore 42 diameter and is inserted therein. The retaining ring 44 has a longitudinal dimension somewhat greater than that of the counterbore 42, and therefore extends slightly therefrom. A locking or latching finger 46 of limited radial dimension extends forwardly or to the right from the ring 44 and is provided with a radially inwardly directing tooth 48. The front edge of the tooth is bevelled at 50 to snap over the collar 22 of the male fitting 12, while the trailing edge comprises a right angle shoulder 52 to latch in place behind the collar 22.

It will be understood that the single finger 46 shown is illustrative in nature only.

The opposite end of the ring 44 is counter bored at 54 and forms with the confronting wall 55 of the counterbore 42 a groove 56 in which is seated an O-ring 58. The O-ring is initially installed in the counterbore 54 before the ring 44 is inserted in the counterbore 42. The ring 44 is held in place by sonic or solvent welding, or by a suitable cement.

A notch 60 is provided in the inner periphery of the ring 44 underlying the finger 46 for molding purposes. Although the inner surface 40 of the female receptacle has been disclosed as having a 1 degree taper similar to the external taper of the male fitting, this is not essential to operation of the connector. The inner surface functionally could be cylindrical, since it is the O-ring that is relied on for sealing.

In order to assemble the female connector 24 with the male fitting 12, it is only necessary to grab the male fitting in one hand and the female connector in the other hand, preferably placing a thumb and one or more fingers against the flange 38, and then to push the two parts together axially. The finger (or fingers) 46 cams out and snaps over the collar 22 providing a positive connection between the parts. A finger tip or finger nail may be placed beneath the bevelled surface 50 of the finger to move the latching tooth out of locking engagement with the collar 22 to permit separation of the endotracheal tube from the connector 24 when surgery and anesthesia have been completed.

Although the invention has been illustrated and described as taking the form of an elbow connector, it will be understood that the connector could be a straight-on end to the flexible conduit.

The specific example of the invention as herein shown and described will be understood as being exemplary. Various changes in structure will no doubt occur to those skilled in the art and will be understood as forming a part of the present invention insofar as they fall within the spirit and scope of the appended claims.

The invention is claimed as follows:

1. A female anesthesiology connector comprising a tubular body having a receiving end, said body having an axial bore extending therethrough, said body having a counterbore in said receiving end, a shoulder in said body between said bore and said counterbore, an insert ring having an inner end, said inner end having a counterbore, a sealing O-ring laid in said insert ring counterbore, said insert ring having its inner end secured within said body counterbore against said shoulder wherein said insert ring counterbore and said shoulder define an inwardly opening circumferential groove having said O-ring therein, and a lock finger on said insert ring having a free end extending longitudinally beyond said tubular body in readily accessible position for manual release, said finger having locking means adjacent said free end for locking engagement with a cooperating part on a male connector.

2. A connector as set forth in claim 1 wherein said tubular body, said insert ring, and said finger are all made of plastic, said finger being of lesser radial thickness than said insert ring, said ring and said finger having aligned outer surfaces, the locking means on said finger comprising a radially inwardly directed tooth, said ring having an inwardly opening recess aligned with said finger and said tooth.

* * * * *